United States Patent [19]

Rowland et al.

[11] Patent Number: 4,728,601
[45] Date of Patent: Mar. 1, 1988

[54] TETRA-AZA INDENE COMPOUNDS

[75] Inventors: David Rowland, Knutsford; Michael E. Dale, Macclesfield; Geoffrey E. Ficken; William E. Long, both of Wilmslow; Andrew W. Yates, Knutsford, all of England

[73] Assignee: Ciba-Geigy AG, Basel, Switzerland

[21] Appl. No.: 846,675

[22] Filed: Apr. 1, 1986

[30] Foreign Application Priority Data

Apr. 12, 1985 [GB] United Kingdom ................ 8509381

[51] Int. Cl.⁴ ......................... G03C 1/02; G03C 1/06; G03C 5/46
[52] U.S. Cl. .................................... 430/565; 430/233; 430/356; 430/611; 430/965; 544/263
[58] Field of Search ............... 430/611, 965, 565, 233, 430/356

[56] References Cited
U.S. PATENT DOCUMENTS 2,566,659  9/1951  Fry ...................................... 430/611
3,418,130 12/1968  Stevens et al. ...................... 430/611

Primary Examiner—Paul R. Michl
Assistant Examiner—Lee C. Wright
Attorney, Agent, or Firm—Wenderoth, Lind & Ponack

[57] ABSTRACT

Tetra-aza indene compounds of the formula

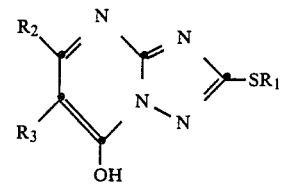

wherein $R_1$ is alkyl or a ring system and $R_2$ and $R_3$ are hydrogen or alkyl.

These compounds are of use as image toners in photographic materials.

3 Claims, No Drawings

TETRA-AZA INDENE COMPOUNDS

The present invention relates to novel tetra-aza indene compounds and to their use in photographic assemblies.

It is well known that certain tetra-aza indene compounds are of use as stabilisers in photographic assemblies, as described, for example, in the book "The Stabilisation of Photographic Silver Halide Emulsions" by E. J. Birr, published by the Focal Press, 1974. We have found new ballasted tetra-aza indene compounds which can be used in photographic materials.

According to the present invention there are provided tetra-aza indene compounds of the formula

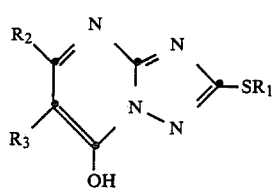

(1)

wherein $R_1$ is alkyl containing 6 to 11 carbon atoms or is a ring system and the groups $R_2$ and $R_3$ are each individually hydrogen or alkyl containing 1 to 4 carbon atoms.

The new compounds of formula (1) are of use as image toners in photographic materials and are of special use in black and white photographic printing paper to impart a neutral tone in the developed silver image.

Suitable compounds of the formula (1) are, for example, those of formulae

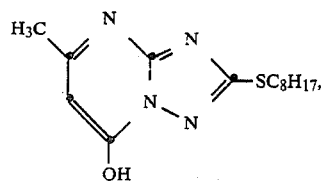

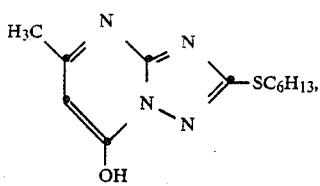

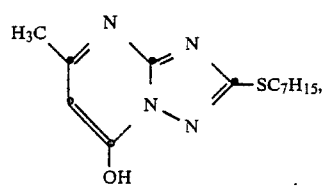

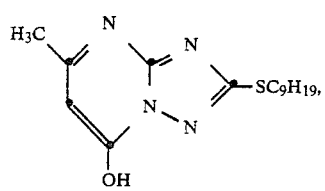

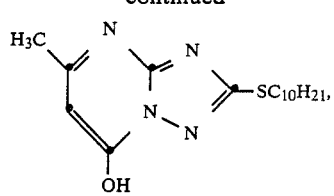

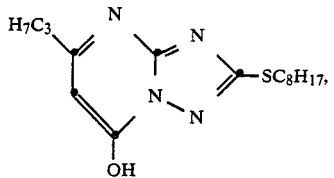

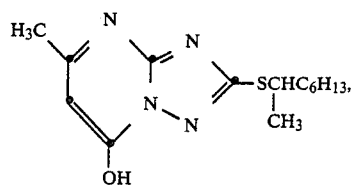

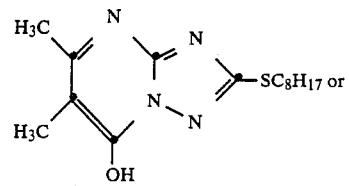

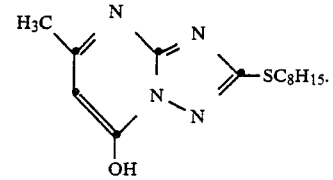

The best image toning is obtained by use of compounds of formula (1) wherein $R_1$ is octyl, nonyl, decyl, cyclohexyl, cycloheptyl or cyclooctyl. Most preferably $R_1$ is normal octyl, normal nonyl or normal decyl.

The substituents $R_2$ and $R_3$ have a limited effect only on the image tonig properties of the compound of formula (1). However for ease of synthesis, $R_2$ is preferably a methyl group and $R_3$ is a hydrogen atom.

Thus, preferably, in the compounds of formula (1) $R_1$ is normal octyl, normal nonyl or normal decyl, $R_2$ is methyl and $R_3$ is hydrogen.

Mostly preferred are the compounds of the formulae

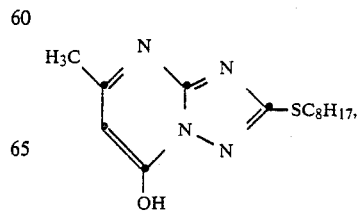

-continued

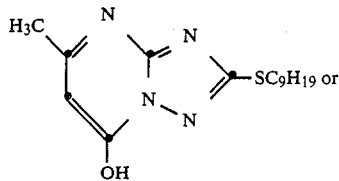

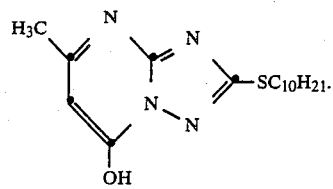

Thus it has been found as is shown in the Examples which follow in the case of a compound of formula (1) in which $R_1$ is a methyl group or a short chain alkyl group, $R_2$ is a methyl group, and $R_3$ is hydrogen there is negligible effect on image tone. Increasing the lenghth of the chain of the group $R_1$ to n-hexyl or n-heptyl gives a weak blue-black toning effect on monochrome printing paper materials. Further increases of the length of the chain of the group $R_1$ to n-octyl, n-nonyl, n-decyl or cyclooctyl groups give a strong effect on image tone, whilst a further increase to a dodecyl group gives only a weak effect again.

The book "The Stabilisation of Photographic Silver Halide Emulsions" by E. J. Birr, published by the Focal Press in 1974 mentions several compounds of use as modifying image tone, especially on pages 167, 168 and 169. Most of these compounds are not ballasted, for example nitrobenzimidazole and benztriazole. Moreover, most of the compounds described have disadvantages associated with their use, for instance often the compounds have adverse sensitometric effects, and in many cases the effect on image tone is unreliable or dependent on certain conditions during coating, hardening, processing or drying of the assembly, and in some cases the compounds are difficult or costly to prepare.

For instance, the tetra-aza indene compound of formula

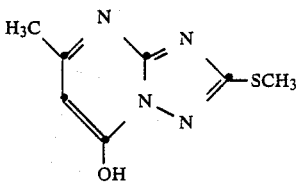

has been described as a blue-black toner in British Patent Specification No. 900,092.

However, this compound is only described for use as an image toner in diffusion transfer processes and has no effect on image tone in conventional photographic systems.

Futaki, Ohyma and Iwasaki in Photographic Science and Engineering 1960, volume 4, page 97 describe tetra-aza indene compounds such as the compound of formula

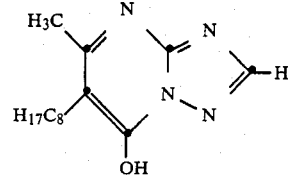

as suitable for modifying image tone.

However, these compounds are only described as being used in liquid photographic emulsions, and their effect on coated and dried layers is not described. Moreover, the compounds of formula (3) are difficult to prepare since the substituted acetoacetates necessary are not commercially available and the synthesis also involves the carcinogenic amino triazole.

The new compounds of formula (1) of the present invention do not suffer from such disadvantages. They are easy to prepare and give reliable blue-black image tones without adverse photographic or sensitomeric effects.

The compounds of formula (1) may be prepared by reaction between a triazole compound of formula

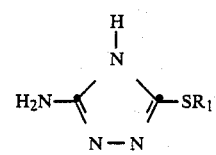

in which $R_1$ has the meaning assigned above with a β-keto ester of formula

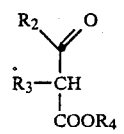

in which $R_2$ and $R_3$ have the meanings assigned above and $R_4$ is an alkyl group, preferably ethyl or methyl.

Preferably, this reaction is carried out in the presence of an acid catalyst, for example acetic acid or sulphuric acid, in a suitable solvent such as methylated spirit.

The intermediate of formula (4) may be prepared by reactio between 3-amino-5-mercapto-1,2,4-triazole with an alkylating agent of formula $R_1X$ where X is a leaving group such as bromide, in the presence of base such as sodium hydroxide, and in a suitable solvent such as methylated spirit.

According to another aspect of the present invention there is provided photographic silver halide material which comprises in at least one silver halide emulsion layer at least one tetra-aza indene compound of formula (1).

Preferably the compound of formula (1) is in each silver halide emulsion layer of the material.

Preferably the amount of the compound of formula (1) present in a silver halide emulsion layer is from 0.5 to 30 g per mole of silver present in the silver halide emulsion.

The toning effect of the tetra-aza indene compound is dependent on its concentration, a greater amount yielding a colder or bluer toner. The actual amount to be added depends on the silver halide material used but sufficient can be used to change a brown warm tone to a neutral tone, but if more is used a distinctly bluish color image may be obtained.

The image toning effect of the presence of the compound of formula (1) in the silver halide emulsion is exhibited with any of the halide compositions used in photographic material for example bromide, chlorobromide, chloride, iodochlorobromide.

The base may be any base of use as a photographic base including paper, polyethylene laminated paper base, film base and white pigment film base.

Preferably the binder for the silver halide crystals is gelatin but any of the other binders commonly used in silver halide materials to completely or partially replace the gelatin may be used for example modified gelatin, albumin or polyvinyl alcohol. A polymer latex may also be present to alter the physical properties of the layer.

Any of the usual additives found in photographic silver halide materials may also be present for example optical sensitising dyes, emulsion stabilisers, gelatin hardening agents and development and storage antifoggants.

Any of the normal silver halide developing agents used to develop exposed silver halide materials may be used to develop the photographic material of the present invention. For example developing solutions which comprise hydroquinone, metol or 1-phenyl-3-pyrazolidinone, whether substituted or not and either alone or in admixture. The developing solution may contain any of the normal ingredients of silver halide developing solutions apart from the silver halide developing agent such as antifoggants, stabilisers, alkali and buffering agents.

The following examples will serve to illustrate the invention.

EXAMPLE 1

Preparation of compound A of formula (1) in which $R_1$ is n-octyl, $R_2$ is methyl and $R_3$ is H.

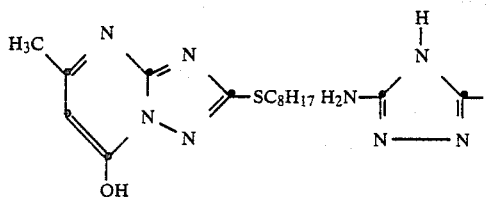

Compound A          Compound B

3-Amino-5-mercapto-1,2,4-triazole (6.5 g), octyl bromide (8.6 ml), and triethylamine (7 ml) were heated under reflux in acetonitrile (100 ml) for 25 hours and then cooled and added to water (200 ml). An oil appears which slowly crystallises on stirring, and was recrystallised from light petroleum (boiling point 80°–100° C.) (100 ml) together with some ethyl acetate. Yield 9.17 g, melting point 94°–96° C.

A sample of compound B, prepared as above (20 g), ethyl acetoacetate (12 ml), and acetic acid (50 ml) were heated under reflux for 5 hours and then allowed to cool. The precipitated solid was filtered off and washed with a little methylated spirit and then recrystallised from ethyl acetate and light petroleum (300 ml), yield 15.9 g, melting point 141°–142° C.

The following compounds of formula (1) were prepared using the same synthetic route:

| Compound | $R_1$ | $R_2$ | $R_3$ | m.p. (°C.) |
|---|---|---|---|---|
| C | $CH_3$ | $CH_3$ | H | 284–287 |
| D | n-$C_6H_{13}$ | $CH_3$ | H | 138–140 |
| E | n-$C_7H_{15}$ | $CH_3$ | H | 139–140 |
| F | n-$C_9H_{19}$ | $CH_3$ | H | 139–141 |
| G | n-$C_{10}H_{21}$ | $CH_3$ | H | 139–140 |
| H | n-$C_{12}H_{25}$ | $CH_3$ | H | 138–139 |
| I | n-$C_8H_{17}$ | n-$C_3H_7$ | H | 138 |
| J | n-$C_8H_{17}$ | $CH_3$ | $CH_3$ | 163–167 |
| K | —$CH(CH_3)C_6H_{13}$ | $CH_3$ | H | 120–127 |
| L | -Cyclo-octyl | $CH_3$ | H | 206–209 |

EXAMPLE 2 (USE EXAMPLE)

A gelatin silver chloro-bromide emulsion containing 55 mole percent silver chloride and 45 mole percent silver bromide and of median crystal size 0.31 μm was prepared using the controlled crystal techniques described in British Patent Specification No. 1,335,925.

This emulsion was desalinated and chemically sensitised by the addition of sodium thiosulphate followed by chemichal ripening at 55° C. until the optimum levels of speed and contrast were obtained.

At this point the emulsion was stabilised by the addition of 0.375 g per mole of silver compound C which as shown below does not act as a cold toner.

The emulsion was subsequently split into several portions and prepared for coating.

To each portion of emulsion was also added 2 g per mole of silver of one of the compounds A and C to L. A control emulsion was given no such addition. All the emulsions were then coated on polyethylene laminated photographic paper base at a silver coating weight of 1.1 g per square meter.

Samples from all these coatings were then exposed to give an even reflectance within the range 38% to 42%, and processed for two minutes at 20° C. in developer of the following composition:

| | |
|---|---|
| Sodium sulphite (anhydrous) | 13.5 g |
| Hydroquinone | 3.3 g |
| Sodium carbonate (anhydrous) | 27 g |
| 1-Phenyl-3-pyrazolidinone | 0.12 g |
| Potassium bromide | 0.7 g |
| Bentriazole | 0.01 g |
| Water to | 1000 ml |

The coatings were then rinsed in water for five seconds and fixed for two minutes at 20° C. in a solution of the following composition:

| | |
|---|---|
| Sodium thiosulphate (anhydrous) | 65 g |
| Sodium metabisulphite | 6 g |
| Sodium sulphite (anhydrous) | 2.5 g |
| Water to | 1000 ml |

The samples were then washed for two minutes in running water and dried using warm air.

After drying the colour of the silver image was measured. Samples with a reflectance between 38% and 42% have been found useful as a means of characterising the colour of the mid-density image. The measured parameters do not vary significantly with this density range.

Measurements were made with a Hunterlab Colorimeter Model D25A-2. The parameters measured were 'a' value which indicates the balance of red and green tint, higher values representing redness, and 'b' value which indicates the balance of blue and yellow tint, higher values representing yellowness. The 'b' value is a measure of the degree of coldness or warmth of the silver image, lower 'b' values indicating bluer tones which have a colder neutral appearance.

The colour values obtained were:

| Compound | Coating No. | 'a' Value | 'b' Value |
|---|---|---|---|
| None | 1 | 0.0 | 2.3 |
| A | 2 | 0.3 | 0.9 |
| C | 3 | 0.0 | 2.3 |
| D | 4 | 0.4 | 1.9 |
| E | 5 | 0.3 | 1.9 |
| F | 6 | 0.6 | 0.2 |
| G | 7 | 0.3 | 0.6 |
| H | 8 | 0.2 | 2.3 |
| I | 9 | 0.3 | 0.6 |
| J | 10 | 0.3 | 0.1 |
| K | 11 | 0.2 | 1.5 |
| L | 12 | 0.2 | 1.2 |

These results show only small changes in 'a' value, indicating that the balance between green and red tint is not significantly changed by the presence of a compound of formula (1). On the other hand there are large changes in 'b' value showing that the coldness or warmth of the image has substantial variation.

The 'b' value of the control coating, measured as 2.3 units, indicates a 'warm' or slightly brown image colour, while the lowest 'b' values measured, around 0.0 to 0.5 units, represent a neutral image colour which is what is required for general purpose photographic papers as those sold under the trade name ILFOSPEED.

Consideration of coatings numbers 1 to 8 shows that when $R_1$ is a methyl group there is no effect on image colour and when $R_1$ is increased to a n-hexyl or n-heptyl group there is a small cold toning effect. However, with n-alkyl groups of eight to ten carbon atoms there is a substantial cold toning effect which peaks with the nonyl substituent. On increasing the alkyl chain length to 12 carbon atoms the cold toning effect is eliminated.

Coatings 9 and 10 show that changes to the other alkyl groups $R_2$ and $R_3$ do not impair the cold effect, indeed in these cases the effect is enhanced. The result of coating 11 shows that $R_1$ can be a branched alkyl chain though in this case the cold toning effect is somewhat reduced. The resulting of coating 12 shows that $R_1$ can be a cyclo-alkyl group though in this case also the cold toning effect is somewhat reduced.

What is claimed is:

1. A photographic silver halide material which comprises at least one silver halide emulsion layer, said material comprising at least one tetra-aza indene compound of the formula

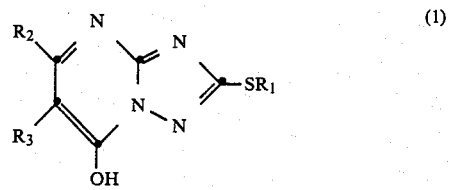

wherein $R_1$ is unsubstituted alkyl containing 6 to 11 carbon atoms, cyclohexyl, cycloheptyl or cyclooctyl and the groups $R_2$ and $R_3$ are each individually hydrogen or alkyl containing 1 to 4 carbon atoms.

2. A photographic silver halide material according to claim 1 wherein the tetra-aza indene compound is present in each silver halide emulsion layer of the material.

3. A photographic silver halide material according to either claim 1 or claim 2 wherein the amount of tetra-aza indene compound present in a silver halide emulsion layer is from 0.5 to 30 g per mole of silver present in the silver halide emulsion.

* * * * *